(12) United States Patent
Wiktor

(10) Patent No.: US 6,923,828 B1
(45) Date of Patent: *Aug. 2, 2005

(54) INTRAVASCULAR STENT

(75) Inventor: Dominik M. Wiktor, St. Petersburg Beach, FL (US)

(73) Assignee: Medtronic, Inc., Minneapolis, MN (US)

( * ) Notice: Subject to any disclaimer, the term of this patent is extended or adjusted under 35 U.S.C. 154(b) by 520 days.

This patent is subject to a terminal disclaimer.

(21) Appl. No.: 09/721,107

(22) Filed: Nov. 22, 2000

Related U.S. Application Data

(63) Continuation of application No. 09/531,097, filed on Mar. 21, 2000, now abandoned, which is a continuation of application No. 07/872,737, filed on Apr. 22, 1992, now Pat. No. 6,113,621, which is a continuation of application No. 07/327,286, filed on Mar. 22, 1989, now Pat. No. 5,133,732, which is a continuation-in-part of application No. 07/109,686, filed on Oct. 19, 1987, now Pat. No. 4,886,062.

(51) Int. Cl.⁷ ............................................... A61F 2/06
(52) U.S. Cl. ..................................... 623/1.15; 623/1.22
(58) Field of Search ............................. 623/1.11, 1.12, 623/1.15, 1.16, 1.17, 1.18, 1.2, 1.22; 606/192, 606/195

(56) References Cited

U.S. PATENT DOCUMENTS

| | | |
|---|---|---|
| 2,070,073 A | 2/1937 | Walton |
| 2,701,559 A | 2/1955 | Cooper |
| 2,854,982 A | 10/1958 | Pagano |
| 2,854,983 A | 10/1958 | Baskin |
| 3,105,492 A | 10/1963 | Jeckel |
| 3,155,095 A | 11/1964 | Brown |
| 3,284,762 A | 11/1966 | Kompanek |
| 3,334,629 A | 8/1967 | Cohn |
| 3,526,005 A | 9/1970 | Bokros et al. |
| 3,540,431 A | 11/1970 | Mobin-Uddin |
| 3,562,820 A | 2/1971 | Braun |
| 3,599,641 A | 8/1971 | Sheridan |
| 3,657,744 A | 4/1972 | Ersek |
| 3,713,175 A | 1/1973 | Weisman |
| 3,714,671 A | 2/1973 | Edwards et al. |

(Continued)

FOREIGN PATENT DOCUMENTS

| | | |
|---|---|---|
| DE | 837122 | 7/1949 |

(Continued)

OTHER PUBLICATIONS

9 Journal of the American College of Cardiology 2 (Supplement A):106A (from Abstracts of the 36.sup.th Annual Scientific Session, American College of Cardiology, New Orleans, Louisiana, Mar. 8-12, 1987), Elsevier (Feb. 1987).

(Continued)

*Primary Examiner*—Ralph A. Lewis

(57) ABSTRACT

A medical device for use in the interior of a body lumen includes a balloon catheter and a radially expandable stent. The stent includes a plurality of zig-zags of a low memory metal formed into a hollow, open-ended cylindrical shape. The individual zig-zags have a curved portion forming a reversing bend which allows the zig-zags to expand and deform as the balloon radially expands the stent. The curved portions of the zig-zags are aligned along the length of the stent in a spaced-apart arrangement with some curved portions attached and others unattached to adjacent zig-zags. The resulting stent is longitudinally flexible throughout its length when unexpanded and is also capable of conforming to a bend in the body lumen when expanded.

21 Claims, 6 Drawing Sheets

U.S. PATENT DOCUMENTS

| | | |
|---|---|---|
| 3,774,596 A | 11/1973 | Cook |
| 3,834,394 A | 9/1974 | Hunter et al. |
| 3,858,441 A | 1/1975 | Comeau |
| 3,868,956 A | 3/1975 | Alfidi et al. |
| 3,874,388 A | 4/1975 | King et al. |
| 3,882,845 A | 5/1975 | Bucalo |
| 3,889,685 A | 6/1975 | Miller, Jr. et al. |
| 3,893,344 A | 7/1975 | Dantlgraber et al. |
| 3,894,974 A | 7/1975 | Hunter et al. |
| 3,952,747 A | 4/1976 | Kimmell, Jr. |
| 3,968,800 A | 7/1976 | Vilasi |
| 3,993,078 A | 11/1976 | Bergentz et al. |
| 4,038,702 A | 8/1977 | Sawyer |
| 4,038,703 A | 8/1977 | Bokros |
| 4,047,252 A | 9/1977 | Liebig et al. |
| 4,056,854 A | 11/1977 | Boretos et al. |
| 4,061,134 A | 12/1977 | Samuels et al. |
| 4,065,816 A | 1/1978 | Sawyer |
| 4,076,285 A | 2/1978 | Martinez |
| 4,080,706 A | 3/1978 | Heilman et al. |
| 4,105,022 A | 8/1978 | Antoshkiw et al. |
| 4,106,129 A | 8/1978 | Carpentier et al. |
| 4,130,904 A | 12/1978 | Whelen |
| 4,140,126 A | 2/1979 | Choudhury |
| 4,159,719 A | 7/1979 | Haerr |
| 4,183,102 A | 1/1980 | Guiset |
| 4,190,909 A | 3/1980 | Ablaza |
| 4,195,637 A | 4/1980 | Gruntzig et al. |
| 4,198,982 A | 4/1980 | Fortner et al. |
| 4,214,587 A | 7/1980 | Sakura, Jr. |
| 4,276,132 A | 6/1981 | Fettel et al. |
| 4,295,464 A | 10/1981 | Shihata |
| 4,299,226 A | 11/1981 | Banka |
| 4,300,244 A | 11/1981 | Bokros |
| 4,313,231 A | 2/1982 | Koyamada |
| 4,319,363 A | 3/1982 | Ketharanathan |
| 4,323,994 A | 4/1982 | Coogler |
| 4,328,811 A | 5/1982 | Fogarty |
| 4,338,942 A | 7/1982 | Fogarty |
| 4,340,046 A | 7/1982 | Cox |
| 4,343,048 A | 8/1982 | Ross et al. |
| 4,343,049 A | 8/1982 | Fettel et al. |
| 4,390,599 A | 6/1983 | Broyles |
| 4,402,307 A | 9/1983 | Hanson et al. |
| 4,403,612 A | 9/1983 | Fogarty |
| 4,448,195 A | 5/1984 | LeVeen et al. |
| 4,479,497 A | 10/1984 | Fogarty et al. |
| 4,483,340 A | 11/1984 | Fogarty et al. |
| 4,493,711 A | 1/1985 | Chin et al. |
| 4,494,531 A | 1/1985 | Gianturco |
| 4,503,569 A | 3/1985 | Dotter |
| 4,512,338 A | 4/1985 | Balko et al. |
| 4,531,933 A | 7/1985 | Norton et al. |
| 4,550,447 A | 11/1985 | Seller, Jr. et al. |
| 4,553,545 A | 11/1985 | Maass et al. |
| 4,560,374 A | 12/1985 | Hammerslag |
| 4,562,596 A | 1/1986 | Kornberg |
| 4,572,186 A | 2/1986 | Gould et al. |
| 4,577,631 A | 3/1986 | Kreamer |
| 4,580,568 A | 4/1986 | Gianturco |
| 4,586,505 A | 5/1986 | Sisson et al. |
| 4,601,713 A | 7/1986 | Faqua |
| 4,604,762 A | 8/1986 | Robinson |
| 4,617,932 A | 10/1986 | Kornberg |
| 4,619,246 A | 10/1986 | Molgaard-Nielsen et al. |
| 4,619,261 A | 10/1986 | Guerriero |
| 4,641,653 A | 2/1987 | Rockey |
| 4,643,184 A | 2/1987 | Mobin-Uddin |
| 4,647,416 A | 3/1987 | Seller, Jr. et al. |
| 4,649,922 A | 3/1987 | Wiktor |
| 4,650,466 A | 3/1987 | Luther |
| 4,655,771 A | 4/1987 | Wallsten |
| 4,660,559 A | 4/1987 | McGregor et al. |
| 4,660,560 A | 4/1987 | Klein |
| 4,665,918 A | 5/1987 | Garza et al. |
| 4,670,734 A | 6/1987 | Caddock |
| 4,673,409 A | 6/1987 | Van Kampen |
| 4,676,241 A | 6/1987 | Webb et al. |
| 4,680,031 A | 7/1987 | Alonso |
| 4,681,110 A | 7/1987 | Wilkor |
| 4,699,611 A | 10/1987 | Bowden |
| 4,704,126 A | 11/1987 | Baswell et al. |
| 4,705,517 A | 11/1987 | DiPisa, Jr. |
| 4,706,671 A | 11/1987 | Weinrib |
| 4,710,181 A | 12/1987 | Fuqua |
| 4,723,549 A | 2/1988 | Wholey et al. |
| 4,731,054 A | 3/1988 | Billeter et al. |
| 4,733,665 A | 3/1988 | Palmaz |
| 4,739,762 A | 4/1988 | Palmaz |
| 4,740,207 A | 4/1988 | Kreamer |
| 4,760,849 A | 8/1988 | Kropf |
| 4,762,128 A | 8/1988 | Rosenbluth |
| 4,767,418 A | 8/1988 | Deininger et al. |
| 4,768,507 A | 9/1988 | Fischell et al. |
| 4,771,773 A | 9/1988 | Kropf |
| 4,775,426 A | 10/1988 | Murley et al. |
| 4,776,337 A | 10/1988 | Palmaz |
| 4,787,899 A | 11/1988 | Lazarus |
| 4,787,900 A | 11/1988 | Yannas |
| 4,793,348 A | 12/1988 | Palmaz |
| 4,794,928 A | 1/1989 | Kletschka |
| 4,795,458 A | 1/1989 | Regan |
| 4,800,882 A | 1/1989 | Gianturco |
| 4,813,925 A | 3/1989 | Anderson, Jr. et al. |
| 4,830,003 A | 5/1989 | Wolff et al. |
| 4,842,575 A | 6/1989 | Hoffman, Jr. et al. |
| 4,848,343 A | 7/1989 | Wallsten et al. |
| 4,856,516 A | 8/1989 | Hillstead |
| 4,870,966 A | 10/1989 | Dellon et al. |
| 4,875,480 A | 10/1989 | Imbert |
| 4,877,030 A | 10/1989 | Beck et al. |
| 4,878,906 A | 11/1989 | Lindemann et al. |
| 4,886,062 A * | 12/1989 | Wiktor |
| 4,892,539 A | 1/1990 | Koch |
| 4,892,541 A | 1/1990 | Alonso |
| 4,893,623 A | 1/1990 | Rosenbluth |
| 4,907,336 A | 3/1990 | Gianturco |
| 4,913,141 A | 4/1990 | Hillstead |
| 4,922,905 A | 5/1990 | Strecker |
| 4,923,464 A | 5/1990 | DiPisa, Jr. |
| 4,950,227 A | 8/1990 | Savin et al. |
| 4,954,126 A | 9/1990 | Wallsten |
| 4,969,458 A | 11/1990 | Wiktor |
| 4,969,890 A | 11/1990 | Sugita et al. |
| 4,986,831 A | 1/1991 | King et al. |
| 4,990,155 A | 2/1991 | Wilkoff |
| 4,994,071 A | 2/1991 | MacGregor |
| 4,998,539 A | 3/1991 | Delsanti |
| 5,002,560 A | 3/1991 | Machold et al. |
| 5,007,926 A | 4/1991 | Derbyshire |
| 5,015,253 A | 5/1991 | MacGregor |
| 5,019,085 A | 5/1991 | Hillstead |
| 5,019,090 A | 5/1991 | Pinchuk |
| 5,026,377 A | 6/1991 | Burton et al. |
| 5,034,001 A | 7/1991 | Garrison et al. |
| 5,035,706 A | 7/1991 | Gianturco et al. |
| 5,037,377 A | 8/1991 | Alonso |
| 5,037,392 A | 8/1991 | Hillstead |
| 5,037,427 A | 8/1991 | Harada et al. |
| 5,041,126 A | 8/1991 | Gianturco |
| 5,059,211 A | 10/1991 | Stack et al. |
| 5,061,275 A | 10/1991 | Wallsten et al. |
| 5,062,829 A | 11/1991 | Pryor et al. |
| 5,064,435 A | 11/1991 | Porter |

| | | | |
|---|---|---|---|
| 5,071,407 A | | 12/1991 | Termin et al. |
| 5,078,726 A | | 1/1992 | Kreamer |
| 5,078,736 A | | 1/1992 | Behl |
| 5,084,065 A | | 1/1992 | Weldon et al. |
| 5,089,005 A | | 2/1992 | Harada |
| 5,089,006 A | | 2/1992 | Stiles |
| 5,092,877 A | | 3/1992 | Pinchuk |
| 5,102,417 A | | 4/1992 | Palmaz |
| 5,104,399 A | | 4/1992 | Lazarus |
| 5,108,416 A | | 4/1992 | Ryan et al. |
| 5,108,417 A | | 4/1992 | Sawyer |
| 5,122,154 A | | 6/1992 | Rhodes |
| 5,123,917 A | | 6/1992 | Lee |
| 5,133,732 A | * | 7/1992 | Wiktor |
| 5,163,958 A | | 11/1992 | Pinchuk |
| 5,192,307 A | | 3/1993 | Wall |
| 5,195,984 A | | 3/1993 | Schatz |
| RE34,327 E | | 7/1993 | Kreamer |
| 5,226,913 A | | 7/1993 | Pinchuk |
| 5,314,444 A | | 5/1994 | Gianturco |
| 5,653,727 A | | 8/1997 | Wiktor |
| 5,902,332 A | | 5/1999 | Schatz |
| 6,066,167 A | * | 5/2000 | Lau et al. |
| 6,066,168 A | | 5/2000 | Lau et al. |
| 6,113,621 A | * | 9/2000 | Wiktor |
| 6,656,219 B1 | * | 12/2003 | Wiktor ..................... 623/1.15 |

FOREIGN PATENT DOCUMENTS

| | | |
|---|---|---|
| DE | 2410933 | 9/1974 |
| DE | 3205942 | 9/1983 |
| DE | 3640745 | 6/1987 |
| EP | 0 183 372 | 6/1986 |
| EP | 0 177 330 | 9/1986 |
| GB | 1205743 | 9/1970 |
| GB | 2092894 | 8/1982 |
| GB | 2135585 | 9/1984 |
| JP | 60-500520 | 4/1985 |
| JP | 61-41444 | 2/1986 |
| SU | 660689 | 5/1979 |
| SU | 764684 | 9/1980 |
| SU | 1217402 | 3/1986 |
| SU | 1457921 | 9/1987 |
| WO | WO 83/03752 | 11/1983 |
| WO | WO 89/01798 | 3/1989 |

OTHER PUBLICATIONS

Baier RE, Dutton RC, "Initial events in interaction of blood with a foreign surface," J Biomed Mater Res Symp 1969; 2: 191-206.

Balko et al., "Transfemoral Placement of Intraluminal Polyurethane Prosthesis for Abdominal Aortic Aneurysm," Journal of Surgical Research 40, 305-309 (1986).

Becker, G.J., et al., "Stimultaneous Angioplasty and Intraluminal Grafting with the Palmaz Expandable Intraluminal Graft," 72.sup.nd Scientific Assembly and Annual Meeting of the Radiological Society of Norht America, Chicago (Nov./Dec. 1996). [Abstract].

Campbell, C.D. et al. "Expanded Microporous Polytetraflouroethylene as a Vascular Substitute: A Two Year Follow-up," 85 Surgery, No. 2, 177-183, St. Louis: C.V. Mosby Co. (Feb. 1979).

Carrasco, C.H., et al., "Expandable Biliary Endoprosthesis: An Experimental Studt," 145 AJR, 1279-1281, Baltimore: American Roentgen Ray Society (Dec. 1985).

Castaneda-Zuniga, W.R., Transluminal Angioplasty, New York: Thieme-Stratton, iii-207 (1983).

Charnsangavej, C., et al., "Endovascular Stent for Use in Aortic Dissection: An In Vitro Experiment," 157 Radiology, 323-324, Easton PA: The Radiological Society of North American (1985).

Charnsangavej et al., "Stenosis of the Vena Cava; Prelimary Assessment of Treatment with Expandable Metallic Stents," 161 Radiology, 295-298 (1986).

Charnsangavej et al, "A New Expandable Metallic Stent for Dialtion of Stenotic Tubular Structures: Experimental and Clinical Evaluation," Houston Medical Journal, vol. 3 (Jun. 1987).

Cimochowski, G., et al., "Greenfield Filter Versus Mobin-Uddin Umbrella," 79 Journal of Thoracic and Cardiovascular Surgery, No. 3, 385-365, St. Louis: C.V. Mosby Co. (Mar. 1980).

Coons, H., et al., "Large-Bore, Long Biliary Endoprosthese (Biliary Stents) for Improved Drainage," 148 Radiology, 89-94, Easton, PA: The Radiological Society of North Americal (Jul. 1983).

Cope, C., "Balloon Dilation of Closed Mesocaval Shunts," 135 AJR, 989-993, Baltimore: American Roentgen Ray Society (Nov. 1980).

Cragg et al., "Nonsurgical Placement of Arterial Endoprostheses: A New Technique Using Nitinol Wire," 147 Radiology, 261-263 (Apr. 1983).

Cragg, A., et al., "A New Percutaneous Vena Cava Filter," 141 AJR 601-604, Baltimore: American Roentgen Ray Society (Sep. 1983).

Cragg, A.H., et al., "Percutaneous Arterial Grafting," 150 Radiology, No. 1, 45-49, Easton PA: The Radiological Society of North America (Jan. 1984).

Culverwell, M. "Angioplasty Stents May Prevent Restenosis," Cardio (Jan. 1987).

Denny, D., et al., "Percutaneous Kimray-Greenfield Filter Placement by Femoral Vein Puncture," 145 AJR, 827-829, Baltimore: American Roengen Ray Society (Oct. 1985).

DePalma VA, Baier, Ford JW, Gott VL, Furuse A, "Investigation of Three Surface Properties of Several Metals and their relation to Blood Compatibility," J Biomed Mater Res Symp 1972; 3:37-75.

Deriu G., et al., "The Rationale for Patch-Graft Angioplasty After Carotid Endarterectomy: Early and Long-Term Follow-Up," 15 Stroke, No. 6, 972-979, Dallas: American Heart Association (Nov. 1984).

DiMassa et al., Abstract: "Maintenance of Longterm Arterial Patency by Implantation of a Metallic Prosthetic Device," Abstract of the 59th Scientific Sessions, AHA, Dallas, pp. 11-363 (1986).

Dorland's Illustrated Medical Dictionary, 26th ed., 1981 pp. 675 & 759, Philadelphia: W.B. Saunders (1981).

Dorros G. et al., "Clinical Research: Angioplasty" Circulation Supplement 1986; 74: 1448; II363. [Abstract].

Dotter, C., et al., "Transluminal Treatment of Arteriosclerotic Obstruction," 30 Circulation, 654-670, Dallas: American Heart Association (Nov. 1964).

Dotter, C., "Interventional Radiology-Review of an Emerging Field," 16 Seminars in Roentgenology No. 1 (Jan. 1981).

Dotter, C., MD et al,. "Technical Developments and Instrumentation: Transluminal Expandable Nitinol Coil Stent Grafting: Preliminary Report," Radiology 147:259-260 (Apr. 1983).

Duprat, Jr. et al., "Flexible Balloon-Expanded Stent for Small Vessels," 162 Radiology, 276-278 (1987).

Duprat et al., "Self-Expanding Metallic Stents for Small Vessels: An Experimental Evaluation," 162 Radiology, No. 2, 469-72, (Feb. 1987).

Edwards, W.S., "Arterial Grafts," 113 Archives of Surgery, No. 9, 1225-1223, Chicago: AMA (Nov. 1978).

Eichelter, P., et al., "Prophylaxis of Pulmonary Embolism," 97 Archives of Surgery, 348-356, Chicago: AMA (Aug. 1968).

Fallone et al., "Elastic Characteristics of the Self-expanding Metallic Stents," Invest. Radiology 23:370-376 (1988).

Fogarty, T.J., et al., "Adjunctive Intraoperative Arterial Dilation: Simplified Instrumentation Technique," 116 Archives of Surgery, 1391-1398, Chicago: AMA (1981).

Fogarty, T.J. et al., "Current Status of Dilatation Catheters and Guiding Systems," 53 The American Journal of Cardiology, No. 12, 97C-100C, New York: Robert T. Brawn (Jun. 1984).

Fogarty, T.J., et al., "Intraoperative Coronary Artery Balloon-Catheter Dilation," 107 American Heart Journal, No. 4, 845-851, St. Louis, C.V. Mosby (1984).

Foubia et al., Abstract: "Intracoronary Stenting of Canine Coronary Arteries After Percutaneous Coronary Angioplasty (PTCA)," Circ. vol. 74, Supp II (Oct. 1986).

Frimberger, E., "Expanding Spiral—A New Type of Prosthesis for the Palliative Treatment of Malignant Esophageal Stenosis," Endoscopy 15, 213-214 (1983).

Gardner, R.J., et al., "The Surgical Experience and a One to Sixteen Year Follow-Up of 277 Abdominal Aortic Aneurysms," 135 American Journal of Surgery, No. 1, 226-230 (Jan. 1978).

Goldstein, H., et al., "Transcatheter Occlusion of Abdominal Tumors," 120 Radiology, No. 3., 539-545, Easton, PA: Radiological Society of North America (Sep. 1976).

Greenfield, L., et al., "A New Intracaval Filter Permitting Continued Flow and Resolution of Emboli," 73 Surgery, No. 4, 599-606, St. Louis: C.V. Mosby (Apr. 1973).

Gunther, R., M.D., et al., "Percutaneous Nephrophyelostomy Using a Fine-Needle Puncture Set," 132 Radiology, No. 1, 228-230, Easton, PA: Radiological Society of North America (Jul. 1979).

Gunther, R., et al., "Vena Caval Filter to Prevent Pulmonary Embolism: Experimental Study," 156 Radiology, No. 2, 315-320, Easton, PA: Radiological Society of North America (Aug. 1985).

Harris-Jones, E.P., et al., " Repositions of Biliary Endoprosthesis with Gruntzig Balloon Catheters," 138 AJR, 771-772, Baltimore: American Roentgen Ray Society (Apr. 1982).

Hickey et al., "In Vivo Angioscopy Following Balloon Angioplasty," Circulation, vol. 74, Supp II (Oct. 1986).

Hoevels, J., et al., "Percutaneous Transhepatic Insertion of a Permanent Endoprosthesis in Obstructive Lesions of the Extrahepatic Bile Ducts," 4 Gastrointestinal Radiology, 367-377, New York: Springer-Verlag (1979).

Honickman, S., et al., "Malpositioned Biliary Endoprosthesis," 144 Radiology, 423-425, Easton, PA: Radiological Society of North America (Jul. 1982).

Hunter, J. et al., "Experimental Balloon Obstruction of the Inferior Vena Cava," 171 Annals of Surgery, No. 2, 315-320, J.B. Lippincott (Feb. 1970).

Inoue, K., et al., "Clinical Application of Transvenous Mitral Commissurotomy by a New Balloon Catheter," 87 J. Thorac. Cardiovascular Surg., No. 3, 394-402, St. Louis, C.V. Mosby (Mar. 1984).

Kan, J.S., et al., "Percutaneous Balloon Valvuloplasty: A New Method for Treating Congenital Pulmonary-Valve Stenosis," 307 N. Engl. J. Med., No. 9, 540-542, Boston: Massachusetts Medical Society (1982).

Kerlan, Jr., et al., "Biliary Endoprostheses: Insertion Using a Combined Peroral-Transhepatic Method." 150 Radiology, No. 3, 828-830, Easton, PA: Radiological Society of North America (1984).

Kerlan, R.K., Jr., et al., "A Simple Method for Insertion of Large Untapered Catheters," 141 AJR, 792, Baltimore: American Roetgen Ray Society (Oct. 1983).

Lababidi, Z. et al., "Percuntatenous Balloon Aortic Valvuloplasty: Results in 23 Patients," 53 Am. J. Cardiol. 194-197, Robert T. Brawn (Jan. 1984).

Lary, B., et al., "The Experimental Use of Steel Mesh Tubes for the Replacement of Arterial Segments", 72 AMA Archives of Surgery, 69-75, Chicago: AMA (Jan. 1956).

Lawrence Jr., D., et al., "Percutaneous Endovascular Graft: Experimental Evaluation," Radiology vol. 163, No. 2, 357-360 (1987).

Lewandowski, B., et al., "The Air-Filled Hepatic Duct: The Saber Sign as an Aid to the Radiographic Diagnosis Pneumobilia," 153 Radiology, No. 2, 329-332, Easton, PA: Radiological Society of North America (Nov. 1984).

Lund, G., et al., "A New Vena Caval Filter for Percutaneous Placement and Retrieval: Experimental Study," 152 Radiology,No. 2, 369-372, Easton, PA: Radiological Society of North America (Aug. 1984).

Lunderquist, A., et al., "Guidewire for Percutaneous Transhepatic Cholangiography," 132 Radiology, No. 1, 228, Easton, PA: Radiological Society of North America (Jul. 1979).

Maass et al, "Radiological Follow-Up of Transluminally Inserted Vascular Endoprotheses: An Experimental Study Using Expanding Spirals," 152 Radiology, 659-663 (1984).

Mirich et al., "Percutaneously Placed Endovascular Grafts for Aortic Aneurysms: Feasiblity Study," Radiology 170: 1033-1037 (1989).

Mobin-Uddin, K., et al., "Caval Interruption for Prevention of Pulmonary Embolism," 99 Archives on Surgery, 711-715, Chicago, AMA (Dec. 1969).

Mobin-Uddin, K., et al., "The Inferior Vena Cava Umbrella Filter," 17 Progress in Cardiovascular Diseases, No. 5, 391-399, Crune & Stratton (Mar./Apr. 1975).

Moenaghan MA, et al., "Tissue Response to Surface-Treated Tantalum Implants: Preliminary Observations in Primates," 13 J. Biomed Mater Res., No. 4, 631-643 (Jul. 1979) [Abstract].

Mullins et al., "Implantation of Balloon-Expandable Intravascular Grafts by Catheterization in Pulmonary Arteries and Systemic Vein," 77 Circulation, No. 1, 188-199 (1988).

Nanda, R., et al., "Effect of Maxillary Osteotomy on Subsequent Craniofacial Growth in Adolescent Monkeys," Am J Orthod (May 1983). [Abstract].

Palestrant, A., et al., "Comparative in Vitro Evaluation of the Nitinol Inferior Vena Cava Filter," 145 Radiology, 351-355, Easton, PA: Radiological Society of North America (Nov. 1982).

Dr. Julio Palmaz's Monograph (1980).

Palmaz, J., et al., "Removable Biliary Endoprosthesis," 140 AJR, 812-814, Baltimore: American Roentgen Ray Society (Apr. 1983).

Dr. Julio Palmaz's Monograph (May 18, 1983).

Palmaz et al., "Expandable Intraluminar Graft: A Preliminary Study," by Radiology, 73-77 (1985).

Palmaz et al., "Expandable Intrahepatic Portacaval Shunt Stents: Early Experience in the Dog," 145 AJR, 821-825 (Oct. 1985).

Palmaz et al., "Atherosclerotic Rabbit Aortas; Expandable Intraluminal Grafting," Radiology, 723-726 (1986).

Palmaz et al., "Expandable Intraluminal Vascular Graft: A Feasibility Study," Surgery, pp. 199-205 (Feb. 1986).

Palmaz, J. et al., "Experimental Balloon Expandable Intraluminal Stenting of Normal and Abnormal Renal Arteries," 72nd RSNA Meeting, Chicago, Illinois, pp. 1-23 [plus figures] (Nov. 1986).

Palmaz et al., "Balloon Expandable Intaluminal Grafting of Normal and Abnormal Renal Arteries: Experimental Study," 72nd Scientific Assembly and Annual Meeting, Radiological Society of North America, Chicago (Nov./Dec. 1986). [Abstract].

Palmaz et al., "Expandable Intrahepatic Portacaval Shunt Stents in Dogs with Chronic Portal Hypertension," 147 AJR; 1251-1254, (Dec. 1986).

Palmaz et al., "Die Intraluminale Stent—Implantation Nach Palmaz," 27 Radiologe; 560-563 (1987).

Palmaz et al., "Normal and Stenotic Renal Arteries: Experimental Balloon-Expandable Intraluminal Stenting," 164 Radiology, No. 3, 705-8 (Sep. 1987).

Palmaz, J., et al., "Balloon Expandable Intra-Arterial Stents: Effect of Anticoagulation on Thrombus Formation," 76 Circulation Supplement, Part II, No. 4, 0108, Dallas: American Heart Association (Oct. 1987). [Abstract].

Papanlcolaou et al., "Insertion of Biliary Endoprosthesis Using a Balloon Dilation Catheter," Gastrointest. Radiol. 10:394-396 (1985).

Pate, J., et al., "A New Form of Vena Caval Interruption," 169 Annals of Surgery, No. 6, 873-880, J.B. Lippincott (Jun. 1969).

Puel, J., et al., "Intravascular Stents to Prevent Restenosis After Transluminal Coronary Angioplasty," 76 Circulation Supplement, Part II, No. 4, 0105, Dallas: American Heart Association (Oct. 1987). [Abstract ].

Rashkind, W.J., et al., "Creation of an Atrial Septal Defect Without Thoracotomy: A Palliative Approach to Complete Transposition of the Great Arteries," 196 JAMA, No. 11, 173-174, Chicago, AMA (Apr.-Jun. 1966).

Ring, E.J., et al., "A simple, Indwelling Biliary Endoprothesis Made From Common Available Catheter Material," 139 AJR, 615-617, Baltimore: American Roentgen Ray Society (Sep. 1982).

Roehm, Jr., et al., "Percutaneous Transcatheter Filter for the Interior Vena Cava," 150 Radiology, No. 1, 255-257, Easton PA: Radiological Society of North America (Jan. 1984).

Roland et al., "Spiral Teflon Stent for Tuboplasty Involving Fimbria," New York Fertility Res. Foundation, NY, Jan. 30, 1970, vol. 36, No. 3, Sep. 1970.

Rollins, N., et al., "Self-Expanding Metallic Stents: Preliminary Evaluation in an Atheroschlerotic Model," 163 Radiology, No. 3, 739-742, Easton, PA: Radiological Society of North America (Jun. 1987).

Rosch, J., et al., "Transjugular-Intrahepatic Portacaval Shunt: An Experimental Work," 121 The American Journal of Surgery, 588-592, New York: Rueben H. Donnelley (May 1971).

Rosch, "Expandable Gianturco-type Wire Stents in Experimental Intraheptic Porta Cava Shunts", Radiology 72.sup.nd Scientific Assembly and Meeting Agenda Chicago: Nov. 30-Dec. 5, 1986, Radiology 161:40 (Nov. 1986).

Rosch, et al., "Expendable Stents in Experimental and Clinical Use," SCIVR 121-124 (1987).

Rosch et al., "Experimental Intraheptic Portacaval Anastomosis: Use of Expandable Gianturco Stents," 162 Radiology, 481-485 (1987).

Rosch et al., "Gianturco Expandable Wire Stents in the Treatment of Superior Vena Cava Syndrome Recurring After Maximum-Tolerance Radiation," Cancer 60:1243-1246 (1987).

Rosch, J., et al., "Modified Gianturco Expandable Wire Stents In Experimental and Clinical Use," Ann. Radiol. vol.31, No. 2, pp 100-103 (1987).

Roubin et al., "Early and Late Results of Intracoronary Arterial Stenting After Coronary Angioplasty in Dogs," 76 Circulation, No. 4, 891-897 (1987).

Rousseau, H., et al., "Percutaneou Vascular Stent: Experimental Studies and Preliminary Clinical Results in peripheral Arterial Diseases," Inter. Angio, 6, 153-161 (1987).

Rousseau et al., "Self-Expanding Endovascular Prosthesis: An Experimental Study," Radiology 164:709-714 (1987).

Schatz et al., "Balloon Expandable Intravascular Grafts," Texas Heart Institute Conference on Invernentional Cardiology (Oct. 1986).

Schatz et al., "Balloon Expandable Intracoronary Stents In Dogs," Circ. vol. 74, Supp II, pp. 11-458 (Oct. 1986).

Schatz, R., et al., "Balloon Expandable Intracoronary Stents in the Adult Dog," 59th Scientific Sessions of the American Heart Association Meeting, Dallas (Nov. 1986).

Schatz, R., et al., "Balloon-Expandable Intracoronary Stents in the Adult Dog," Circulation 76(2):450-7 (Aug. 1987).

Schatz, R., et al., "New Technology in Angioplasty: Balloon-Expandable Intravascular Stents," 2 New Developments in Medicine, No. 2, 59-75 (Sep. 1987).

Schatz, Richard A., Palmaz, Julio C., "Intravascular Stents for Angioplasty," Cardio, Dec. 1987.

Selmon et al., Abstract: "Histophatholigic Comparison of Initial and Restenosis Lesions with Tissue From Transluminal Atherectomy," Circulation, vol. 74, Supp. II (Oct. 1986).

Semb, B.K.H., et al., "Balloon Valvulotomy of Congential Pulmonary Value Stenosis with Tricuspid Valve Insufficiency," 2 Cardiovascular Radiology, 239-241, New York: Springer-Verlag (1979).

Sigwart et al., Abstract: "Initial Experience With a New Approach to Stenting of Peripheral and Coronary Arteries," Texas Heart Institute Conference on Interventional Cardiology, p. 59 (Oct. 1986).

Sigwart et al., "Intravascular Stents to Prevent Occlusion and Restenosis After Transluminal Angioplasty," 316 The New England Journal of Medicine, No. 12, pp. 701-706 (Mar. 19, 1987).

Sigwart, U. et al., "One Year of Percutaneous Coronary Stenting," 76 Circulation Supplement, Part II, No. 4, 0104, Dallas: American Heart Association (Oct. 1987).

Simon, M., et al., "A Vena Cava Filter Using Thermal Shape Memory Alloy" 125 Radiology, 89-94, Easton, PA: Radiological Society of North America (Oct. 1977).

Smith, D., et al., "Safe and Effective Catheter Angiography Through Prosthetic Vascular Grafts," 138 Radiology, No. 2, 487-488, Easton, PA: Radiological Society of North America (Feb. 1981).

Solberg, S., et al., "Cold Induced Endothelial Cell Detachment in Human Saphenous Vein Grafts," 28 Journal of Cardiovascular Surgery, No. 5, 571-575, Minerva Medica (Sep.-Oct. 1987).

Stack, Richard, MD, "A New Highly Flexible Balloon-Expandable Endovascular Stent: Initial Experimental Results and up to Six Months Follow-Up," Duke University Med. Center, Durham, NC Laser One Mtg., May 11-13, 1989.

Strecker et al,. "A New Vascular Balloon-Expandable Prosthesis—Experimental Studies and First Clinical Results," Journal of Interventional Radiology, 3:59-62 (1985).

Teplick, S.K., et al., "A New Biliary Endoprosthesis," 141 AJR, 799-801, Baltimore: American Roentgen Ray Society (Oct. 1983).

Trent et al., Abstract: "An Expandable Intravascular Stent for the Maintenance of Luminal Patency," presented at Fourth Annual Vascular Fellows Abstract Presentation on Apr. 28, 1988.

Uchida et al., "Modifications of Gianturco Expandable Wire Stents," AJR 150:1185-87 (1988).

Wallace et al., "Tracheobronicial Tree: Expandable Metallic Stents in Experimental and Clinical Applications," 158 Radiology, 309-312 (1986).

White et al., "A New-Percutaneous Balloon Expandable Stent [Abstract]," 61 st Scientific Session of the American Heart Association (Nov. 1988).

Wright et al., "Percutaneous Endovascular Stents; An Experimental Evaluation," 156 Radiology, 69-72 (1985).

Yoshioka et al., "Self-Expanding Endovascular Graft: An Experimental Study in Dogs," AJR 151:673-676 (Oct. 1988).

*Wiktor v. Pinchuk* Interference Proceeding (Civil No. 97-2459)—Testimony by Dominik Wiktor, Oct. 20, 1999, pp. 346-432.

*Wiktor v. Pinchuk* Interference Proceeding (Civil No. 97-2459)—Testimony by Dominik Wiktor, Nov. 1, 1999, pp. 443-478.

Dominik Wiktor Affidavit, Jun. 15, 1990 regarding U.S. Appl. No. 07/327,286.

Dominik Wiktor Affidavit, Jan. 28, 1992 regarding U.S. Appl. No. 07/327,286.

* cited by examiner

INTRAVASCULAR STENT

CROSS REFERENCE TO RELATED APPLICATIONS

This is a continuation of Ser. No. 09/531,097 filed Mar. 21, 2000, now abandoned, which in turn is a continuation of Ser. No. 07/872,737 filed Apr. 22, 1992, now U.S. Pat. No. 6,113,621, which in turn is a continuation of Ser. No. 07/327,286 filed Mar. 22, 1989, now U.S. Pat. No. 5,133,732, which in turn is a continuation-in-part of Ser. No. 07/109,686 filed Oct. 19, 1987, now U.S. Pat. No. 4,886,062.

FIELD OF THE INVENTION

This invention relates to intravascular implants for maintaining vascular patency in humans and animals. The present invention comprises an open-ended wire formed device of basically cylinrical shape and made of a softer-then spring type metal and fitted over an inflatable element of a typical balloon type catheter such as described in U.S. Pat. No. 4,195,637 and U.S. Pat. No. 4,402,307. The wire formed device is intended to act as a permanent prosthesis stent and is implanted transluminarely. Specifically, this invention is characterized by the ability of said intravascular stent to be enlarged radially after having been introduced percutaneously, transported transluminarely and positioned at desired location. In additional this invention relates to a method whereby a permanent prosthesis stent is implanted at the same time the angioplasty procudure is being performed. This invention is particularly useful in transluminar implantation of a stent in the field of cardiology and especially in the case of coronary angioplasty to prevent restenosis.

BACKGROUND OF THE INVENTION

In my U.S. Pat. No. 4,649,992 a device is described in combination with a catheter which is basically a compression spring retained between a partially inflated balloon and an abuttment immediately behind the balloon on the catheter shaft. The intent is to transport the spring prosthesis in this manner to the desired location and then after a successful angioplasty procedure release said spring prosthesis by totally evacuating said balloon, thus allowing said spring prosthesis to expand linearly and stay in place while the balloon catheter is withdrawn. This method is quite simple and its simplicity is very attractive; however, it has some drawbacks. One and foremost is the fact that the spring has a fixed diameter and as such is unable to fully conform to the inside wall of the vessel which at times is quite tortuous and thus could conceivably create a somewhat turbulant flow of blood, and possible thrombosis could in some cases result. Other patents, e.g. U.S. Pat. No. 4,553,545 teaches a different method where a relatively complex mechanical rotating device and co-axial cables are employed to achieve the necessary means to change the diameter of the implanted stent to a larger dimension at the point of implant. Still other patents, e.g. U.S. Pat. No. 3,868,956 describes a method wherein a temperature responsive metallic device is used and expanded after implant using external heat sources. All of the above mentioned devices present drawbacks of various magnitudes including blood coagulation and possible thrombosis and considerable complexity of procedure.

In angioplasty procedures at this time, in many cases restenosis occurs soon thereafter, which requires a secondary procedure or a surgical bypass operation. The implanted prosthesis as described herein will preclude such additional procedures and will maintain vascular patency indefinitely.

Depending on the size used, the stent according to this invention can also be efficacious in other similar applications, such as: repairs of aneurysms, support of artificial vessels or liners of vessels, initial repairs of dissections and mechanical support to prevent collapsing of dialated vessels. Still many other and similar applications will be satisfied by this invention without departing from the basic prewise and concept.

This stent and the metod of its use particularly allows a single procedure to combine the essential angioplasty and a simultaneous implant of a permanent prosthesis designed and intended to prevent restenosis and further complications arising therefrom, also reducing the risk factor and trauma for the patient.

Another use of stents is for aortic dissection.

In the case of aortic dissection, especially a type III dissection of the descending aorta, there is no intravascular stent or prosthesis available, which is both long and flexible enough to repair a typical dissection extending the entire length from the point of origin down to the aortic bifurcation. Also, for the repair of the most difficult and most dangerous dissection, namely the type I which is that of the ascending aorta and the aortic arch, no stent is available today which could be used and be implanted intraluminarely for non-surgical repair of such a dissection. Most intravascular prosthesis and stent available today are of limited length and diameter and are especially limited in terms of flexibility and more specifically in terms of longitudinal flexibility unable to conform to tight bends and adhere to the walls of the intima and at the same time be flexible to stretch and move with each heartbeat such as experienced in the aortic arch.

Therefore, most such cases are treated medically. If surgery is necessary, it often requires the use of hypothermia and cardiopulonary bypass. Surgical procedures of this type involve high risk to the patient, a highly skilled team of cardiovascular surgeons and sophisticated equipment, because it requires the replacement of the affected region with an interpositional graft. High mortality and morbidity are associated with surgery in this region. This is especially true for the elderly and other poor candidates for a major surgery. The cost associated with such a surgical procedure is also very high.

Prior to the development of this invention, there has been no intravascular stent which would satisfy the following conditions necessary to contemplate a non-surgical repair of a dissecting aorta:

a) To be long enough to extend from the base of the aortic arch down to the aortic bifurcation.
b) To be flexible longitudinally throughout its length.
c) To be radially expandable easily, a small section at a time using common dilatation balloon or similar expanding device designed for that purpose.
d) To be radially expandable to various diameters and to conform to tortuous conditions of a diseased aorta.
e) To be non-obstructive to all branches.
f) To be clearly visible on Floroscope both during deployment and post-operatively to visibly ascertain its condition, location and efficacy.
g) To be implantable permanently, retrograde and be able to completely obliterate a false lumen of a dissection and to maintain patency of the main lumen as well, as the patency of all side branches throughout its length.

Other reference publications:
1. Self-Expanding Metalic Stents for Small Vessels *Radiology* 1987-162.469–472.
2. Flexible Balloon-Expandable Stent for Small vessels, *Radiology*, January 1987.
3. Intravascular Stents to Prevent Occlusion and Restenosis After Transluminar Angioplasty, *N.E.J. of M.*, Mar. 19, 1987.
4. U.S. Pat. No. 4,580,568, Percutaneous Endovascular Stent.
5. U.S. Pat. No. 4,503,569, Transluminarely Placed Expandable Graft Prosthesis, Dotter 1985.
6. U.S. Pat. No. 4,649,992, Catheter Arrangement Having a Variable Diameter Tip and Spring Prosthesis, Wiktor 1987.
7. U.S. Pat. No. 4,681,110, Catheter Arrangement and Blood Vessel Liner, Wiktor 1987.

All of the above references describe and teach various methods of providing or otherwise offering and introducing stents of different types and designs for applications similar to the one described herein in this invention.

SUMMARY OF THE INVENTION

The improvement of this invention over other similar devices such as cited in patents above, and specifically my previus invention described in U.S. Pat. No. 4,649,992, is the ability of the device of this invention to allow for and to maintain a very low profile and a small frontal area, so very important for purposes of percutaneous insertion. Thus the stent of this invention can be inserted into and be transported via a standard #8F Guiding Catheter such as USCI Cat. #006128, while using standard procedures and methods. Once on location, the stent can be expanded radially to a diameter larger than initially introduced; a ratio of =2½:1 can easily be achieved with a wire diameter of 0.008 and initial stent diameter of 0.075. The expanded larger diameter will conform to the inside of the vessel and maintain intimate contact with the inside wall. The stent of this invention is characterized by the low memory level of the relatively easily deformable metal used for the wire.

The configuration of stent 1, shown in FIG. 1, is such that the wire 2 is intially preformed into a two-dimensional zig-zag form 3, basically creating a flat expandable band 3*a*. The zig-zag pattern can vary as to its shape and tightness of the reversing bends, but for reasons of simple description a typical sinusoidal form is chosen to depict this band's construction.

In order to create the stent 1, and to have it assume an initial configuration as shown in FIG. 1, also a subsequently radially expanded condition as shown in FIG. 5, a length of preformed band 3*a* is wrapped on a suitable mandrel 4 in a manner similar to that of winding a simple helical spring again as shown in FIG. 1. Care is taken to form the wire band 3*a* flat around the mandrel 4 with little or no tension to prevent premature linear expansion of band 3*a*.

Once the zig-zag band 3*a* is wound into a cylindrical shape, it is removed from the mandrel 4, and is placed over a suitable variable diameter device such as an inflatable balloon 5 typically used for angioplasty procedures as shown in FIG. 2. A suitable forming tool (not shown) is used to tighten the stent over the balloon; manual operation of squeezing the stent over the balloon is also acceptable.

A controlled radial expansion of the stent is accomplished by the force generated by the inflating balloon. When acted upon by the inflating balloon, the stent of this invention being characterized by the zig-zag preformed wire band 3*a* subsequently formed into an open-ended cylindrical shape, is by design and intent capable to expand radially.

The radial expansion in effect is achieved by controlled deformation and tension applied to the sinusoidal pattern of the preformed wire band 3*a*. The low memory metal used for the fabrication of the wire formed stent assures, that the radially expanded stent stays expanded thus fulfilling is preimary intent and function. Other advantages of this invention over those mentioned earlier Ref. 1 through 7, are the inherent post-expansion radial rigidity and linear flexibility, an excellent combination for an intravascular and especially intracoronary stent. In the case of intracoronary application, an overriding factor being the ability of allow for an extremely low profile and a very small frontal area so very essential for initial transluminal introduction and transportation through a standared 8F guiding catheter.

A major object of this invention is the provision of a preformed flexible wire stent which allows easy radial expansion and subsequent retention of the radially expanded shape well anchored within a vessel. Still anther object of this invention is the simplicity of its application, especially with respect to angioplasty, where one procedure accomplishes two distinct functions: In combination with the balloon it compresses the plaque, thus creating a recannalized lumen as characterized by angioplasty, and deploys and implants a permanent prosthesis within the newly created and recannalized lumen to prevent possible reclosure and restenosis thus allowing free flow of blood indefinitely. Both functions are performed simultaneously and with a single insertion of the catheter.

There is a need for a means to restrain an extra long stent from excessive stretching. This invention includes means for preventing a longitudinal overstretch of the stent, particularly during the initial introduction into the vessel where several constrictions occur. The introduction of the stretch limiting means quarantees a constant and uniform pitch of the helical wire formed coil throughout the entire length of the stent both in its non-expanded and especially in its expanded condition and still maintains full flexibility. The longitudinal stretch limiting means can take several forms including a straight wire placed on the outside of the tubular shaped stent spotwelded to each individual coil or alternately using a simple suture thread and tying each coil to the next. Another method found acceptable is to arrange the sinusoidal wave shape pattern where one wave shape out of a series is longer and can be bent to catch the wave of the adjacent coil.

The invention includes means for restraining coils of the helix from longitudinal movement relative to each other. In other words, means are provided for restraining lengthwise stretch of the coil. To one embodiment, the means includes a single lengthwise wire attached, for example, by welding to loops of the coil. In another embodiment, the loop of the coil is hooked over an adjacent loop to restrain longitudinal movement.

DESCRIPTION OF THE PREFERRED EMBODIMENT

For purposes of better and clearer understanding of this invention, reference is made to FIGS. 1–6. The preferred embodiment of this invention is shown and described in an application for angioplasty; however, it is understood that other applications not specifically mentioned herein are ossible and no limitations in scope of this invention are intended or implied without departing from the basic principles of this invention.

Figure 1:
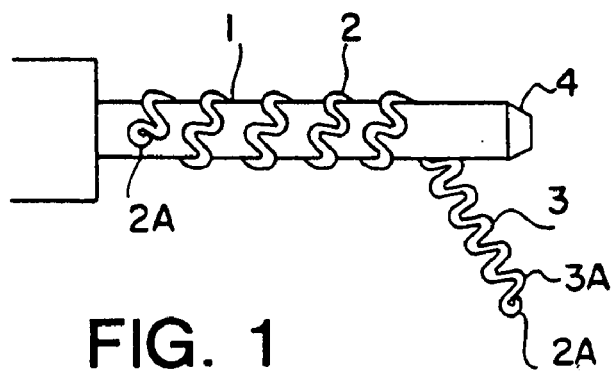
FIG. 1 is a side elevation of a preferred embodiment of a stent according to this invention being wound on a mandrel.

FIG. 1 shows the details of construction of the prosthesis stent 1, hereafter called stent, which is basically of a hollow open-ended cylindrical shape. Stent 1 is basically a tubular shape of coiled preformed wire band typically wound on a suitable mandrel 4. The wire is made of drawn low-memory level material such as stainless steel, titanium ASTM F63-83 Grade 1 or high carat gold K 19–22. Copper alloy typically 110 when properly coated with polyester or Teflon® can also be used. Titanium and gold are biologically compatible and inert and requires no special treatment.

Figure 2:
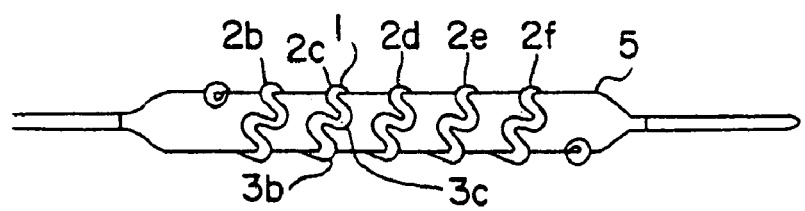
FIG. 2 is a side elevation showing an overall view of a stent prosthesis fitted over a deflated balloon.
Figure 5:
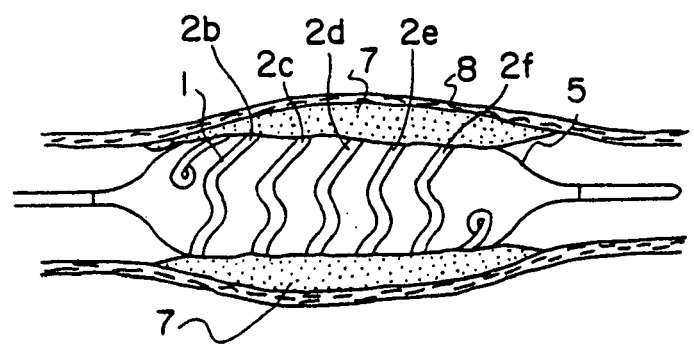
FIG. 5 is similar to FIG. 4, the balloon inflated, and the stent radially expanded, illustrating the preferred method of an angioplasty procedure coupled with a simultaneous deployment and implantation of a permanent prosthesis stent.
Figure 6:
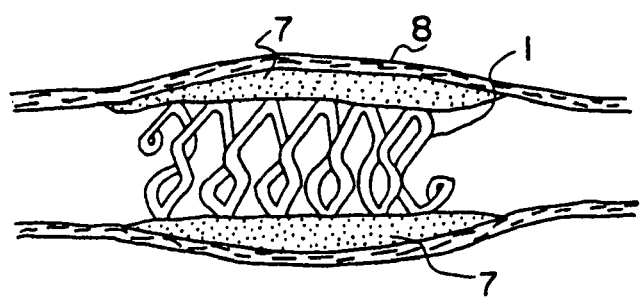
FIG. 6 is a view similar to FIG. 5 showing the prosthesis stent implanted and plaque compressed and retained after removal of the balloon.

In FIG. 2, it is shown that the stent 1 is centrally located and positioned with respect to the length of balloon 5 and that flat preformed wire band 3a turns are evenly spaced so that when stent 1 is expanded as shown in FIG. 5 and FIG. 6, stent 1 will provide even support inside vessel 8, and be able to resist external loading.

Figure 3:
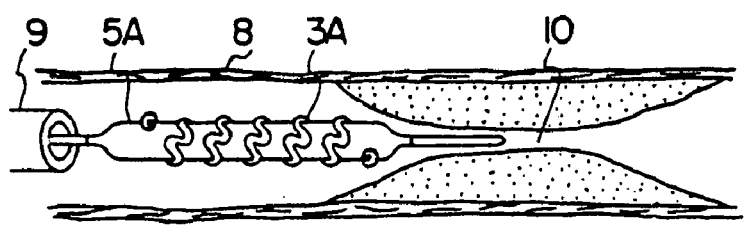
FIG. 3 shows the balloon and stent assembly advanced within a vessel, approaching a partial occlusion.

In FIG. 3, it is shown how balloon and stent assembly 5a emenate from guiding catheter 9 inside vessel 8 and is advanced towards partial occlusion 10.

Figure 4:
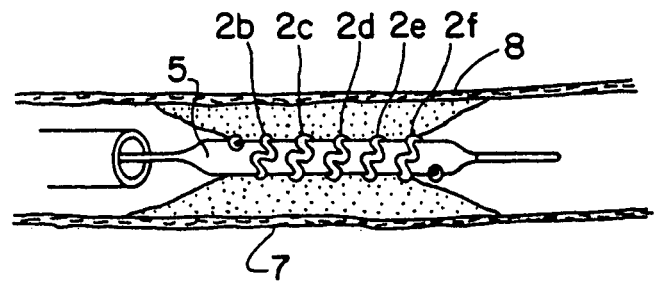
FIG. 4 is similar to FIG. 3 showing the balloon and stent assembly inside a partially occluded vessel.

In FIG. 4, it is shown how balloon and stent assembly 5a are located inside occlusion 10 within arter 8, balloon 5 still being deflated. Once positively placed within occlusion 10, balloon 5 is inflated using standard angioplasty procedures and techniques. As balloon 5 expands, so does the stent 1 as shown in FIG. 5. The expanding balloon 5 together with stent 1 compresses the plaque 7, said plaque remains compressed and stent 1 retains said plaque 7 and prevents possible reocclusion. Angioplasty procedure complted, balloon 5 is deflated and withdrawn leaving stent 1 firmly implanted within vessel 8. Previously occluded vessel 8 is now completely recannalized and patency is restored.

FIG. 6 shows stent 1 firmly implanted and imbedded in compressed plaque 7, providing both adequate support as well as a smooth lumen void of all protrusions, a very desirable feature and condition, since any protrusions are conductive to turbulent blood flow and potential formation of thrombosis.

To test the viability of this novel principle of stent construction, a polyester-coated copper wire of 0.008 diameter was preformed into a zig-zag pattern 3 as shown in FIG. 1 to form a band 3a. This band was subsequently wound into a tubular shape with ends curled into tight loops 2a to prevent sharp ends of wire 2 from perforating balloon 5. The tubular stent was placed over a 3.5 mm PTCA 20/3.5T balloon made by SciMed and fitted tightly over said balloon. The balloon and stent assembly was fed through an 8F guiding catheter into a silastic thin-wall tubing approximately 3 mm inside diameter and balloon was inflated with a standard 10 cc syringe using plain water. The expansion of the stent was observed and documented on video. Several subsequent tests of similar nature also using larger balloons typically MeadoxSurgimed A/S Cat. No. 700720 10 mm dia. and Medi. tech balloon 12 mm dia. were used with a stent made of polyester-coated copper wire 0.014" dia. All tests showed near perfect expansion and "bench-type" implantations. Further experiments showed that multiple stents can be used in tandem. In fact, a typical balloon and stent assembly can be fed right through a previously implanted and expanded stent and be implanted downstream ahead of the previously implanted stent. A distinct advantage in real life situations.

Experimental laboratory tests on animals are now being conducted. Initial results are very encouraging and promising. Both intracoronary and intraaortic stents are being investigated at this time, a complete protocol is being prepared.

Five stents recently implanted in small arteries of pigs and expanded to 3.5 mm have successfully maintained 100% patency for several weeks and as of this date continue to do so.

In sparate experiment, a previously aortic dissection has been stopped by expanding a 10 mm diameter stent within said dissection.

Figure 7:
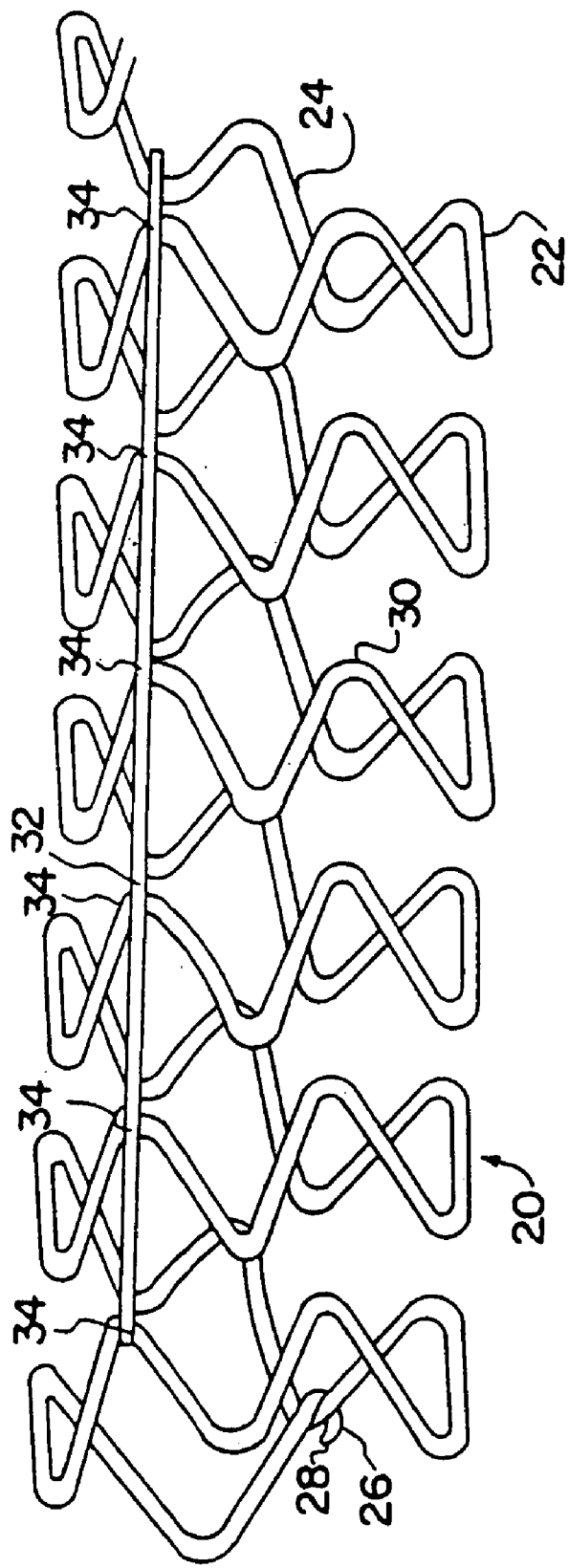
FIG. 7 shows the stent with one type of a longitudinal over-stretch limiting means.

The embodiment of the present invention involving means for preventing longitudinal overstretching is illustrated in FIG. 7. Stent 20 has a generally cylindrical body 22 formed by winding wire 24 in the cylindrical shape, as discussed above. Wire 24 has an end 26 which has a loop 28 hooked over wire 24.

Wire 24 has been formed with zig-zags or waves 30, as in the embodiments discussed above. A longitudinal wire 32 is attached, preferably by welding, to waves 30 of wire 24 at points 34.

Wire 32 prevents stent 20 from expanding along the longitudinal axis of wire 32. Radial expansion of the cylindrical body 22 is accomplished by stretching waves 24, as in the embodiments discussed above.

The structure of FIG. 7 is particularly suitable for long stents which may be more susceptible to stretching. One example is in the case of aortic dissections.

Figure 8:
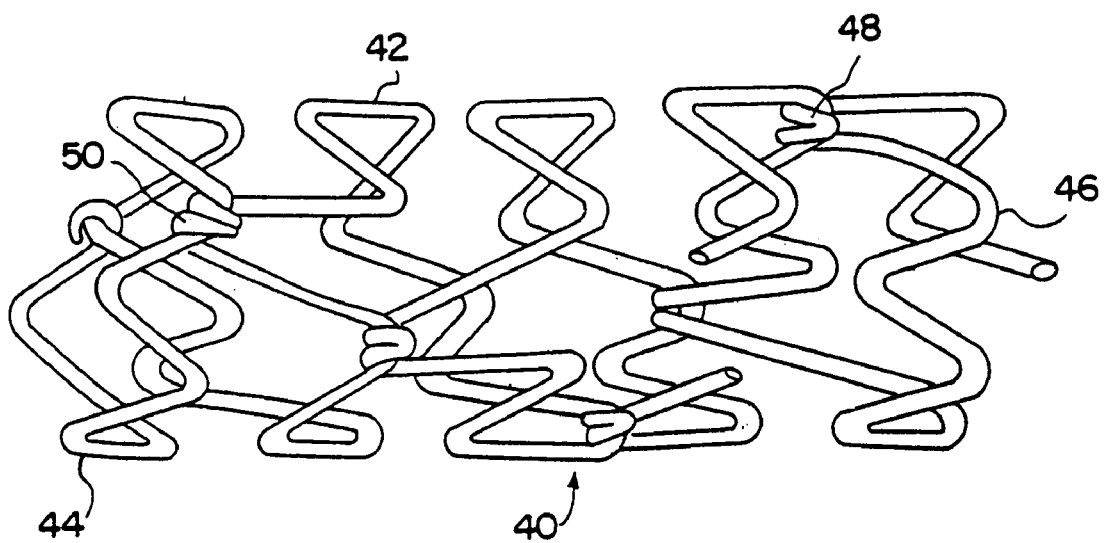
FIG. 8 shows the stent yet with another means to prevent longitudinal over-stretch.

In FIG. 8, it is illustrated an alternative embodiment of means for preventing longitudinal overstretch in a stent constructed according to the present invention. Stent 40 has a generally cylindrical body 42 formed of wire 44. Wire 44 has zig-zags or waves 46.

Certain of waves 46 are longer than others, such as waves 48. In this embodiment, one out of four of waves 46 is elongated as is wave 48.

Elongated waves 48 are bent to form a loop or hook 50. Each hook 50 is looped over a wave 46 adjacent. The engagement of hooks 50 with previous waves 48 prevents longitudinal spread of the cylindrical body 42 of stent 40.

Figure 9:
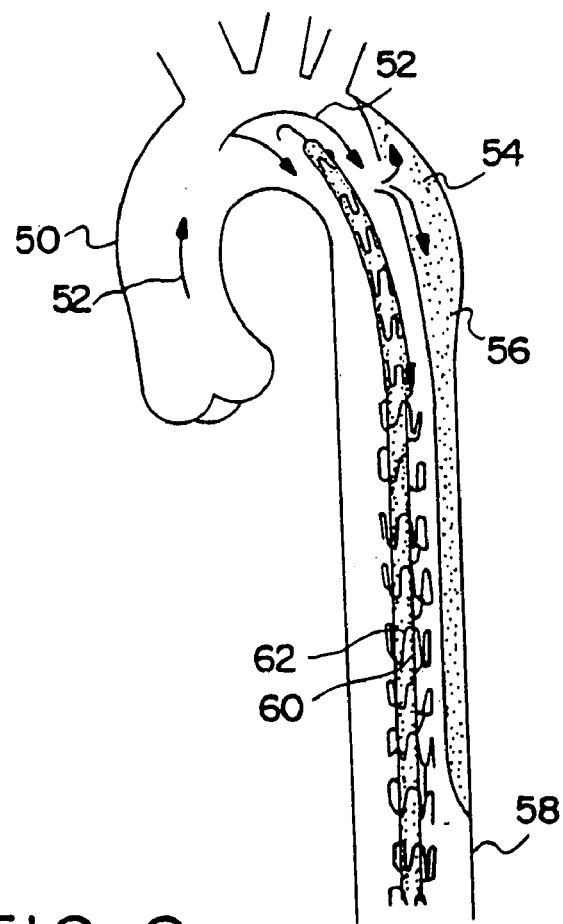
FIG. 9 shows a cross-sectional view of a typical dissection of the descending aorta including a false lumen and the expanding device and stent assembly advanced into position for first expansion.
Figure 10:
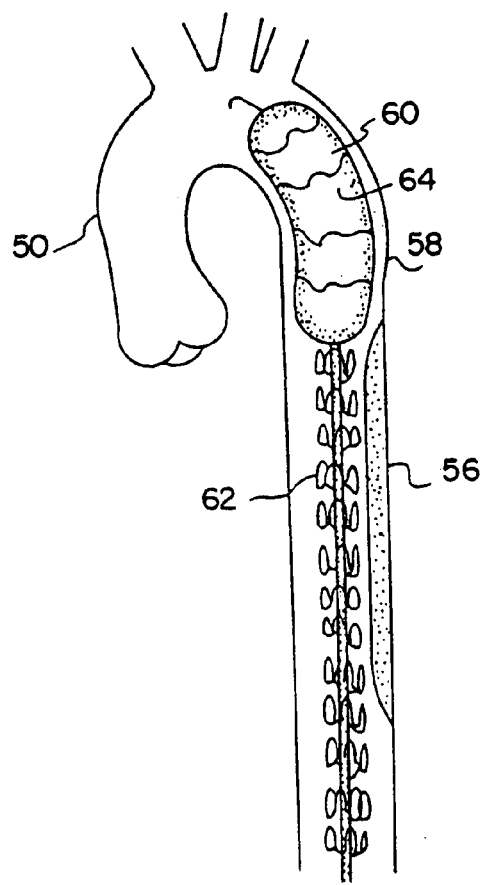
FIG. 10 shows the same cross-section of the aorta as in FIG. 9 with the flexible balloon pressurized with radio-opaque fluid and expanded.

In FIG. 9, a typical type III aortic dissection is illustrated where the aorta 50 is depicted in a cross-sectional view, and the flow of blood is shown by arrows 52. Blood partially enters the origin of dissection 54, creating a false lumen 56 by delaminating the aortic wall 58. The expanding device such as balloon 60 and stent assembly 62 is shown in a side elevation view inside the aorta 50. Balloon 60 is advanced to the point of origin of dissection 54. Balloon 60 transports extra long stent 62 and positions it within the aorta 50 for initial steps of repair. In FIG. 10, balloon 7 is shown filled with radiopaque liquid. Balloon 60 expands the stent 63 into a nearly straight wire coil 64, forcing the false lumen 56 to regress and at this point to re-laminate the aortic wall 58.

Figure 11:
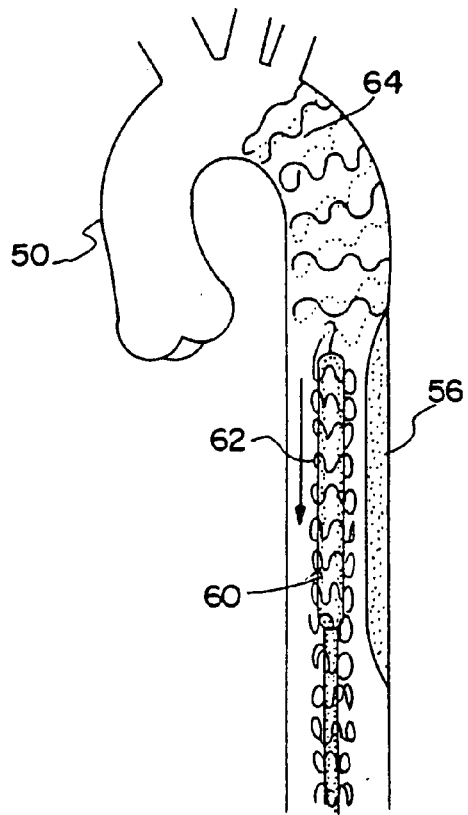
FIG. 11 shows the aorta of FIG. 10, showing the first part of the stent fully expanded, origin of dissection obliterated and expanding device repositioned for next sequential expansion.
Figure 12:
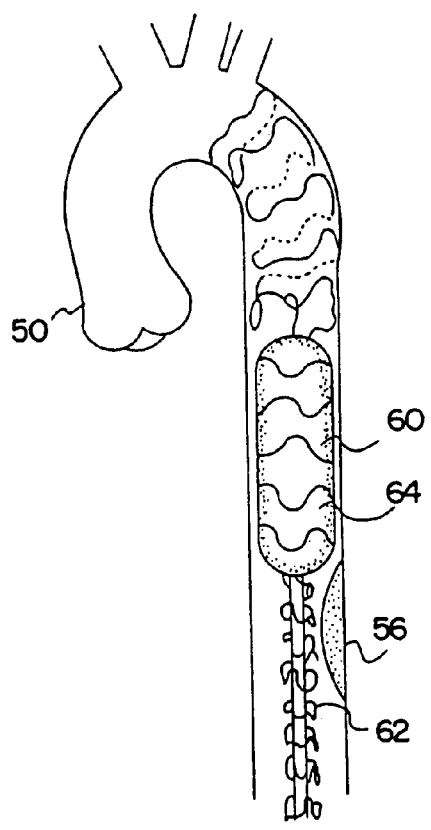
FIG. 12 depicts the next sequential expansion of the stent after FIG. 11.

FIG. 11 illustrates the expanding device 60 and stent 62 after the first stage of stent implant successfully completed, in a deflated and deactivated mode being repositioned for the next sequential procedure to expand the next portion of stent and to obliterate the next section of said false lumen 56. FIG. 12 illustrates the next portion of said false lumen 56 being obliterated by the expanding stent similar to that shown in FIG. 12.

Figure 13:
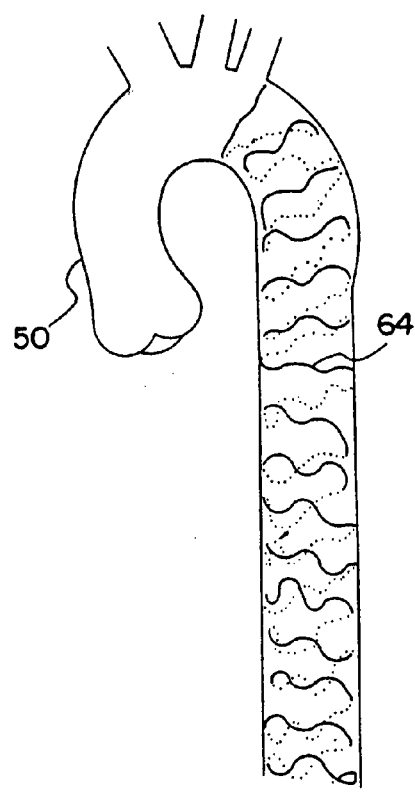
FIG. 13 shows the stent fully expanded and implanted, false lumen obliterated and type III aortic dissection repaired, and expanding device withdrawn, procedure completed.

Finally, FIG. 13 illustrates the entire length of the aorta 50 having been fitted and lined with a long flexible stent 62, said stent 62 being firmly implanted the false lumen completely obliterated and aortic dissection type III fully repaired.

For situations where a long stent may be subjected to longitudinal stretching, either during insertion or during physiologic movement, stents constructed according to the present invention improve upon the prior art by including means for preventing longitudinal stretch. While this improvement has been disclosed in terms of particular embodiment, the prevention of longitudinal stretch by coil-type stents is a desirable goal and is facilitated by this invention.

What is claimed is:

1. An intravascular stent, comprising:
a generally cylindrical body including a helically coiled wire, wherein said helically coiled wire has generally sinusoidally-shaped waves;
wherein said generally cylindrical body is capable of radially expanding.

2. The intravascular stent of claim 1, wherein said helically coiled wire is a low memory metal.

3. The intravascular stent of claim 1, wherein said generally sinusoidally-shaped waves have a generally uniform amplitude.

4. The intravascular stent of claim 1, wherein said helically coiled wire generally forms a series of adjacent rows of said sinusoidally-shaped waves, wherein said sinusoidally-shaped waves of each row have a generally uniform amplitude.

5. The intravascular stent of claim 4, wherein at least one of said sinusoidally-shaped waves of a first row is a longer wave, wherein said longer wave has a larger amplitude than another sinusoidally-shaped wave of said first row.

6. The intravascular stent of claim 5, wherein said larger wave contacts an adjacent second row.

7. The intravascular stent of claim 5, wherein said larger wave of said first row extends beyond a point of a sinusoidally shaped wave of an adjacent second row that is closest to said first row.

8. The intravascular stent of claim 1, wherein a first portion of said stent is capable of being expanded within a human vasculature in a first expanding procedure and a second portion of said stent is capable of being expanded within said human vasculature in a second expanding procedure.

9. The intravascular stent of claim 8, wherein said first portion of said stent is positioned tandem to said second portion of said stent.

10. The intravascular stent of claim 8, wherein, when said first portion is previously implanted and expanded, said second portion is capable of being fed through said first portion and subsequently expanded.

11. The intravascular stent of claim 10, wherein said second portion is expanded downstream from said first portion.

12. The intravascular stent of claim 1, wherein a portion of said stent is capable of being expanded between an aortic arch and an aortic bifurcation of a human.

13. The intravascular stent of claim 1, wherein a position of said stent within a human vasculature is visible on a fluoroscope.

14. An intravascular stent, comprising:
a helically shaped stent body including a wire coiled into a helical shape, wherein said wire comprises a series of undulations, wherein the stent body may be expanded from a first delivery diameter to a second implanted diameter;
wherein said helically shaped stent body generally forms a series of adjacent rows of said undulations;
wherein said undulations of each of said adjacent rows have a generally uniform amplitude;
wherein at least one of said undulations of a first row is a longer undulation, wherein said-longer undulation has a larger amplitude than said generally uniform undulations of said first row;
wherein said larger undulation of said first row extends beyond a point of an undulation of an adjacent second row that is closest to said first row;
wherein a first section of said stent is capable of being expanded within a human vasculature in a first expanding procedure and a second section of said stent is capable of being expanded within said human vasculature in a second expanding procedure;
wherein at least a portion of said stent is capable of being expanded between an aortic arch and an aortic bifurcation of a human; and
wherein a position of said stent within said human vasculature is visible on a fluoroscope.

15. The intravascular stent of claim 14, wherein at least part of said stent is radially expanded by a balloon of a balloon of a balloon catheter.

16. The intravascular stent of claim 14, wherein said stent is mounted on a balloon of a balloon catheter assembly and expanded to said second diameter upon inflation of said balloon.

17. The intravascular stent of claim 14, wherein said helically coiled wire is a low memory metal.

18. The intravascular stent of claim 14, wherein, when said first section is previously implanted and expanded, said second section is capable of being fed through said first section and subsequently expanded.

19. The intravascular stent of claim 18, wherein said second section is expanded downstream from said first section.

20. The intravascular stent of claim 14, wherein said larger undulation contacts an adjacent second row.

21. An intravascular stent, comprising:
a generally cylindrical body including a helically coiled wire, wherein said helically coiled wire has generally sinusoidally-shaped waves;
wherein said generally cylindrical body is capable of radially expanding;
wherein said cylindrical body generally forms a series of adjacent rows of said generally sinusoidally-shaped waves;
wherein said generally sinusoidally-shaped waves of each of said adjacent rows have a generally uniform amplitude;
wherein at least one row includes a longer wave, wherein said longer wave has a larger amplitude than said generally uniform amplitude of said generally sinusoidally-shaped waves of said row.

\* \* \* \* \*